United States Patent [19]
Desai et al.

[11] Patent Number: 5,618,559
[45] Date of Patent: Apr. 8, 1997

[54] METHOD OF MAKING MODIFIED-RELEASE METRONIDAZOLE COMPOSITIONS

[75] Inventors: Subhash Desai, Grayslake; Alan M. Mancini, Indian Head Park; Steven C. Schumann, Elgin, all of Ill.

[73] Assignee: G.D. Searle & Co., Chicago, Ill.

[21] Appl. No.: 445,309

[22] Filed: May 19, 1995

Related U.S. Application Data

[62] Division of Ser. No. 187,568, Jan. 27, 1994.

[51] Int. Cl.$^6$ ............... A61K 9/22; A61K 9/16; A61K 47/32
[52] U.S. Cl. .......... 424/468; 424/487; 424/501; 427/2.15; 427/213
[58] Field of Search ................ 424/486, 487, 424/501, 468; 427/213, 2.15

[56] References Cited

U.S. PATENT DOCUMENTS

| | | | |
|---|---|---|---|
| 2,944,061 | 7/1960 | Jacobs et al. | 260/309 |
| 4,351,825 | 9/1982 | Sothmann et al. | 424/19 |
| 4,892,738 | 1/1990 | Takagishi et al. | 424/468 |
| 4,927,639 | 5/1990 | Ghebre-Sellassie et al. | 424/497 |
| 4,954,350 | 9/1990 | Jones et al. | 424/493 |

OTHER PUBLICATIONS

Baichwal, M.R. et al., *Indian Journal of Pharmaceutical Sciences* 2, 48–51 (1980).
Braybrook, J.H. et al., *Drug Design and Delivery* 6, 73–86 (1990).
Chemtob, C. et al., *Int. J. Pharm.* 29, 1–7 (1986).
Chemtob, C. et al., *Int. J. Pharm.* 29, 83–92 (1986).
Chiba, N. et al., *Am. J. of Gastroenterol.* 87, 1716–1727 (1992).

(List continued on next page.)

Primary Examiner—Edward J. Webman
Attorney, Agent, or Firm—Fitzpatrick, Cella, Harper & Scinto

[57] ABSTRACT

Pharmaceutical compositions having a modified release profile for once daily dosing of metronidazole, methods for making the pharmaceutical compositions, and methods for treating a microbial infection with once daily dosing of the pharmaceutical compositions of the invention are provided. The compositions given once daily exhibit substantial bioequivalence to immediate release metronidazole given three times per day. The compositions of the invention comprise:

(a) a first portion of metronidazole which is about 59 wt % to about 79 wt % metronidazole;

(b) about 1.5 wt % to about 3.0 wt % of an aqueous insoluble poly(meth)acrylic acid ester copolymer which is aqueous permeable, aqueous expandable and pH-independent;

(c) about 0.1 wt % to about 2.0 wt % detackifier;

(d) 0 to about 23 wt % of a first aqueous soluble pharmaceutical diluent;

(e) 0 to about 23 wt % of a second aqueous soluble diluent which is suitable for forming a pharmaceutical tablet when compressed with the granules of (a), the second aqueous soluble diluent being the same as or different from the first aqueous soluble diluent;

(f) 0 to about 20 wt % of a second portion of metronidazole;

(g) 0 to about 0.2 wt % glidant; and (h) 0 to about 2 wt % lubricant;

wherein the composition comprises metronidazole containing granules comprising (a), (b), (c) and (d), wherein the sum of the weight percentages of metronidazole provided by (a) and (f) is between about 72 wt % and about 79 wt %, and wherein the sum of the weight percentages of the aqueous soluble diluent provided by (d) and (e) is between about 16 wt % and about 23 wt %.

9 Claims, 5 Drawing Sheets

OTHER PUBLICATIONS

Eudragit NE30D, "Application in the Production of Pharmaceutical Preparations" Info ED–I/e, Rohm Pharma Product Literature.

Eudragit NE30D, "Data Sheet" Info ED–2/e, Rohm Pharma Product Literature.

Eudragit NE30D, "Standard Sheet" Info ED–7/e, Rohm Pharma Product Literature.

Eudragit NE30D, "Technical Application Pamphlet" Info ED–11/e, Rohm Pharma Product Literature.

Eudragit NE30D, "Technical Application Pamphlet" Info ED–12/e, Rohm Pharma Product Literature.

Fauvelle, F. et al., *Fundam. Clin. Pharmacol.* 34, (4), 181 (1989).

Hentschel, E. et al., *New England J. of Medicine* 328, (5) 308–312 (1993).

Lugo–Miro, V. et al., *JAMA* 268, (1) 92–95 (1992).

Mandal, T.K. et al., *Indian Drugs* 23, (7) 400–403 (1986).

Read, N.W. et al., *CRC Critical Reviews in Therapeutic Drug Carrier Systems* 4, (3) 222–263 (1987).

METHOD OF MAKING MODIFIED-RELEASE METRONIDAZOLE COMPOSITIONS

This is a divisional Application of co-pending application Ser. No. 08/187,568, filed on Jan. 27, 1994.

FIELD OF THE INVENTION

This invention relates generally to metronidazole containing pharmaceutical compositions and particularly to modified release metronidazole compositions which, when taken once daily, release a therapeutically effective amount of metronidazole over a 24 hour period.

BACKGROUND OF THE INVENTION

The use of metronidazole, 1-(2-hydroxyethyl)-2-methyl-5-nitroimidazole, has long been known for the treatment of trichomoniasis and more recently for the treatment of bacterial vaginosis. There are currently at least two effective ways to treat trichomoniasis or bacterial vaginosis with the administration of a metronidazole composition. In the first method, a single, large dose (~2 grams) of metronidazole is given as a bolus to the patient. The single treatment is clinically effective. A major drawback to the administration of a single large dose of metronidazole is occurrence of significant and undesirable side effects such as nausea.

A second and more generally accepted treatment entails orally administering 250 mgs of metronidazole three times a day for a period of 7 days. The lower dosages of metronidazole over a period of a week significantly reduce the occurrence and severity of side effects. However, patient compliance is a problem since patients can inadvertently forget to take one or more doses during the course of treatment, causing the plasma metronidazole levels to drop to below an acceptable therapeutic level for a period of several hours or more.

The use of metronidazole is also known for the treatment of various other conditions, including amebiasis (acute amebic dysentery), and *Helicobacter pylori* infections associated with duodenal ulcer disease, see, e.g., D. Graham, et al., *Annals of Internal Medicine*, 115, 266–269 (1991).

In order to reduce the number of daily doses of metronidazole needed to treat a microbial infection, while maintaining the benefits of making bioavailable effective amounts of the drug over an extended time period, it would be desirable to be able to deliver a therapeutically effective amount of metronidazole in a once daily dose.

Effectively maintaining acceptable bioavailability of metronidazole for up to 24 hours with a single dose and without increased side effects relative to the conventional multiple dose regimen cannot be accomplished simply by increasing the amount of active drug in a single dose. Metronidazole is aqueous soluble and is rapidly absorbed by the bloodstream. Metronidazole is also rapidly cleared from the bloodstream. Thus, merely administering increased amounts of immediate-release metronidazole results in a rapid peak, followed by a rapid decline in metronidazole levels. Such a profile is undesirable because of side effects caused by high peak levels of metronidazole. Also, the rapid clearing of the drug does not permit plasma metronidazole to remain at acceptable levels for 24 hours.

On the other hand, adding amounts of excipients in ratios typical of conventional modified release formulations which are presently available would result in a tablet which is too large for oral administration. For example, 750 mg of metronidazole represents at least about a 2-fold greater amount of active ingredient than is presently available in other pharmaceutical compositions which are available in modified release form. Moreover, metronidazole itself is not readily compressible, which presents a significant problem with respect to forming modified release tablets.

Thus, there is a need to be able to provide a modified release metronidazole composition which is capable of delivering acceptable bioavailability for up to 24 hours. The composition should be readily compressible such that the entire dose may be provided in a single tablet suitable for oral administration. In order to keep the size of a single tablet in the range of about 1000–1100 mg, while providing about 750 mg of metronidazole, a minor amount of excipient (less than about 30% by weight) must be capable of imparting both compressibility properties (for tabletting) and modified release properties (for bioavailability). Heretofore, there has not been a modified release oral tablet dosage of metronidazole which is suitable for once daily dosing, even though metronidazole has been an accepted therapeutic treatment for trichomoniasis for over 25 years.

SUMMARY OF THE INVENTION

The present invention provides pharmaceutical compositions for once daily dosing of metronidazole having substantial bioequivalence to immediate release metronidazole given three times per day. The compositions of the present invention comprise greater than 70% metronidazole and less than 30% excipient, yet, surprisingly, are capable of being tabletted and of providing modified release of metronidazole for up to 24 hours. The compositions of the invention comprise metronidazole containing granules and pharmaceutically acceptable excipients. The compositions comprise:

(a) a first portion of metronidazole which is about 59 wt % to about 79 wt % metronidazole;

(b) about 1.5 wt % to about 3.0 wt % of an aqueous insoluble poly(meth)acrylic acid ester copolymer which is aqueous permeable, aqueous expandable and pH-independent;

(c) about 0.1 wt % to about 2.0 wt % detackifier;

(d) 0 to about 23 wt % of a first aqueous soluble pharmaceutical diluent;

(e) 0 to about 23 wt % of a second aqueous soluble diluent which is suitable for forming a pharmaceutical tablet when compressed with the granules of (a), the second aqueous soluble diluent being the same as or different from the first aqueous soluble diluent;

(f) 0 to about 20 wt % of a second portion of metronidazole;

(g) 0 to about 0.2 wt % glidant; and (h) 0 to about 2 wt % lubricant;

wherein the composition comprises metronidazole containing granules comprising (a), (b), (c) and (d), wherein the sum of the weight percentages of metronidazole provided by (a) and (f) is between about 72 wt % and about 79 wt %, and wherein the sum of the weight percentages of the aqueous soluble diluent provided by (d) and (e) is between about 16 wt % and about 23 wt %.

A presently preferred modified release metronidazole composition comprises 74.05 wt % metronidazole, 8.22 wt % hydrous lactose, 2.47 wt % Eudragit® NE 30 D (solids), 1.23 wt % talc, 0.03 wt % simethicone emulsion, 12.90 wt % anhydrous lactose (direct tablet grade), 0.10 wt % colloidal silicon dioxide, and 0.99 wt % magnesium stearate.

The present invention also includes a method for making a composition of the invention, which method comprises producing metronidazole containing granules in a fluid bed granulation step employing aqueous insoluble poly(meth)acrylic acid ester copolymer as the retard agent. The use of poly(meth)acrylic acid ester copolymer as a retard agent unexpectedly yields granules which provide both modified release characteristics useful for once daily oral administration of metronidazole and compressibility characteristics which allow the compositions of the invention to be compressed into tablet form.

The present invention also entails a method for treating an infection caused by a microorganism which is susceptible to metronidazole, which method comprises administering to a patient having the infection an effective amount of a composition of the invention once daily for a number of days sufficient to eliminate or resolve the infection.

DETAILED DESCRIPTION OF THE INVENTION

In one of its aspects the invention provides modified release, metronidazole-containing compositions which permit a slow release of metronidazole into the bloodstream over a 24 hour period. The pharmaceutical compositions of the present invention comprise:

(a) a first portion of metronidazole which is about 59 wt % to about 79 wt % metronidazole;

(b) about 1.5 wt % to about 3.0 wt % of an aqueous insoluble poly(meth)acrylic acid ester copolymer which is aqueous permeable, aqueous expandable and pH-independent;

(c) about 0.1 wt % to about 2.0 wt % detackifier;

(d) 0 to about 23 wt % of a first aqueous soluble pharmaceutical diluent;

(e) 0 to about 23 wt % of a second aqueous soluble diluent which is suitable for forming a pharmaceutical tablet when compressed with the granules of (a), the second aqueous soluble diluent being the same as or different from the first aqueous soluble diluent;

(f) 0 to about 20 wt % of a second portion of metronidazole;

(g) 0 to about 0.2 wt % glidant; and (h) 0 to about 2 wt % lubricant;

wherein the composition comprises metronidazole containing granules comprising (a), (b), (c) and (d), wherein the sum of the weight percentages of metronidazole provided by (a) and (f) is between about 72 wt % and about 79 wt %, and wherein the sum of the weight percentages of the aqueous soluble diluent provided by (d) and (e) is between about 16 wt % and about 23 wt %.

The compositions of present invention release greater than about 90%–98% of their total metronidazole content at a controlled rate over a 24-hour period. The $C_{max}$ and AUC attained after a single dose are comparable to the $C_{max}$ and AUC values which are achieved by thrice daily oral administration of 250 mg immediate release Flagyl® (G. D. Searle & Co., Skokie, Ill. 60077). As used herein the term "$C_{max}$" means the maximum plasma metronidazole concentration achieved after oral administration of metronidazole. The terms "AUC" or "area under the curve" mean the total amount of metronidazole absorbed by the bloodstream in a predetermined time, generally 24 hours. AUC is a measure of bioavailability which is calculated by integrating plasma metronidazole levels with respect to time.

The term "granules" or "metronidazole-containing granules" as used herein refers to particles produced in a granulation process, which particles comprise metronidazole, poly(meth)acrylic acid ester copolymer, a detackifying agent and preferably an aqueous soluble diluent.

As used herein, all percentages for ingredients are weight percentages, based on the total weight of the pharmaceutical composition, unless otherwise stated. In this respect, it should be noted that the pharmaceutical compositions of the invention are defined as comprising metronidazole containing granules. The granules are blended with certain excipients to produce the pharmaceutical compositions. The major constituent of the granules is metronidazole (i.e., the "first portion of metronidazole"). Accordingly, it will be appreciated that while a first portion of metronidazole is present in an amount up to 79% by weight, with respect to the total weight of the pharmaceutical composition, the granules may comprise up to about 98 wt % of metronidazole (i.e., "first portion"), depending upon the amount of other constituents in the granules. In particularly preferred embodiments of the invention, the granules comprise about 85 wt %–90 wt % metronidazole with respect to the total weight of the granules.

The compositions of the present invention may comprise, optionally, a second portion of metronidazole which is present in an amount of up to 20% by weight. This optional second portion of metronidazole is not utilized in forming the granules, but is mixed in with the granules after they are made. The addition of a second portion of metronidazole is referred to in the Examples herein as being added "neat." The second portion of metronidazole, if added, typically augments the release profile of the compositions of the invention such as by increasing the $C_{max}$ attained.

The synthesis of metronidazole is well known, for example as shown in U.S. Pat. No. 2,944,061. Metronidazole is also commercially available from Farchemia, S.p.A. (Treviglio, Italy) as well as from a variety of other commercial sources. It is presently preferred to mill the metronidazole (first portion and second portion, if any) to a particle size of about 40 mesh or smaller.

Metronidazole containing granules further comprise a poly(meth)acrylic acid ester copolymer as a modified-release agent or retard agent. Poly(meth)acrylic acid ester copolymers which are contemplated for use in the compositions of the invention are pH-independent, aqueous insoluble, aqueous permeable and aqueous expandable, such as those copolymers which are commercially available under the name Eudragit® NE30D from Röhm Pharma (Weiterstadt, Germany). By "pH-independent" it is meant that the copolymers are substantially insoluble in gastric juices, intestinal juices and water. By use of the term "aqueous permeable" is meant that aqueous solutions can pass through pores in the structure of the copolymer. By the term "aqueous expandable" it is meant that the copolymer composition is capable of swelling in an aqueous solution. Eudragit® NE30D copolymers have an average molecular weight of about 800,000 daltons. The compositions of the present invention comprise from about 1.5% by weight to about 3.0% by weight, more preferably from about 1.9% to about 2.5% by weight of a poly(meth)acrylic acid ester copolymer.

Metronidazole containing granules desirably, but not necessarily, further comprise a first aqueous soluble diluent. Among the pharmaceutically acceptable, first aqueous soluble diluents which may be used are lactose, sucrose, dextrose, mannitol, sorbitol, and the like. The first aqueous soluble diluent may comprise up to 23% by weight of the total weight of the pharmaceutical compositions of the invention. It is presently preferred that the first aqueous soluble diluent is present in an amount of from about 5% to about 11% by weight, more preferably from about 6% to about 9% by weight, based on the total weight of the pharmaceutical composition. A particularly preferred first aqueous soluble diluent is hydrous lactose.

It should be appreciated that, inasmuch as the amount of first aqueous soluble diluent employed is incorporated in the granulation process, the amount of first aqueous soluble diluent used, if any, reduces proportionately the amount of metronidazole which may granulated, and thus the number of tablets which may be produced in a single batch.

Since metronidazole containing granules comprising poly(meth)acrylic acid ester copolymer are characteristically tacky, the granules should also comprise an effective amount of a detackifying agent. Suitable detackifying agents, which may be present in effective amounts of from about 0.1% to about 2% by weight, include talc, magnesium stearate, calcium sulfate, glyceryl monostearate, and the like. Finely particulated talc (e.g., 500 mesh) is a preferred detackifying agent.

A presently preferred method for preparing metronidazole containing granules employs fluidized bed granulation. In conventional fluidized bed granulation methods, dry particles of the active ingredient and diluent are suspended in a rising air column and substantially continuously sprayed with a liquid which binds the particles so as to gradually build-up granules as they are suspended in the air column. One advantage of fluidized bed granulation is that it produces dry granules. It may be desirable, although not necessary, to include an effective amount of an antifoam agent (e.g., 0.01 wt %–0.05 wt % simethicone emulsion) in the liquid suspension which is sprayed during the fluid bed granulation process.

After the granulation process is completed, an effective amount of glidant (e.g., about 0.01%–0.2% by weight or more) may be added to the produced granules, if desired, to improve flow characteristics of the mixture, thereby facilitating transfer of the mixture during the manufacturing steps. Several pharmaceutically acceptable glidants are well known to those of ordinary skill in the art. A presently preferred glidant is colloidal silicon dioxide.

In a preferred embodiment, compositions of the present invention comprise a second aqueous soluble diluent, which may be the same as or different from the first aqueous soluble diluent. The second aqueous soluble diluent is an excipient which is blended with the produced granules and which may impart good compressibility, hardness and friability qualities to the compositions of the invention. Examples of second aqueous soluble diluents, include lactose, sucrose, dextrose, mannitol, sorbitol and the like. These pharmaceutical diluents are well known and commercially available in forms which provide desirable compressibility traits (e.g., direct tablet grade (DTG) anhydrous lactose). The compositions of the invention may comprise up to about 23% by weight, more preferably from about 8% to about 18% by weight, and most preferably from about 12% to about 17% by weight of the second aqueous soluble diluent. A presently preferred second aqueous soluble diluent is anhydrous lactose (direct tablet grade). While the first aqueous soluble diluent and the second aqueous soluble diluent may each comprise up to 23% by weight of the compositions of the invention, importantly, the sum of the weight percentages of the first and the second aqueous soluble diluents should be from about 16% to about 23% based on the total weight of the compositions.

The compositions of the present invention may be conventionally compressed into tablets after the metronidazole containing granules are mixed in with the above-described excipients. It is presently preferred that each tablet comprise between about 600 mg and about 1000 mg of metronidazole, more preferably about 750 mg of metronidazole, so as to provide a once daily dosage of metronidazole suitable for administration for a period of several days. It will be appreciated, however, that the compositions may be tabletted into smaller weight units if it were desired to administer more than one tablet at a time.

To facilitate mechanical release of the tablets from the tablet press after compression, an effective amount of a pharmaceutically acceptable lubricant, as is well known in the art, may be added to the compositions. It is presently preferred to use magnesium stearate in an amount of from about 0.1% to about 2.0% by weight.

In another of its aspects, the present invention entails a method for making a modified release metronidazole tablet which is capable of delivering, in a single oral dosage, a therapeutically effective amount of metronidazole over a 24 hour period. The method of the invention comprises the steps of:

(a) contacting in a fluid bed granulator, under conditions suitable for producing granules, (1) a dry mixture comprising from about 59 to about 79 parts by weight of a first portion of metronidazole and optionally up to 23 parts by weight of a first aqueous soluble diluent with (2) an aqueous suspension comprising from about 1.5 to about 3.0 parts by weight of an aqueous insoluble, pH-independent, aqueous expandable polymethacrylic acid ester copolymer, and an effective amount of a detackifying agent;

(b) combining the granules produced in step (a) with an effective amount of a pharmaceutically acceptable glidant;

(c) if necessary, particle-sizing the mixture of (b) to provide a mixture with a substantially uniform particle size suitable for compressing into tablet form;

(d) optionally blending the mixture with up to about 20 parts by weight of a second portion of metronidazole;

(e) blending the mixture with up to 23 parts by weight of a second aqueous soluble diluent and an effective amount of a pharmaceutically acceptable lubricant; and (f) compressing a predetermined amount of the blended mixture of step (e) to produce a tablet.

By use of the phrase "particle-sizing" with respect to a mixture comprising metronidazole granules is meant processing a blended mixture which may have a wide distribution of particle sizes to yield a mixture having a substantially uniform particle size. Milling and sieving procedures, used alone or in combination, are well known in the art for achieving a mixture having a uniform particle size within a predetermined size range (e.g., 20 mesh).

Figure 1:
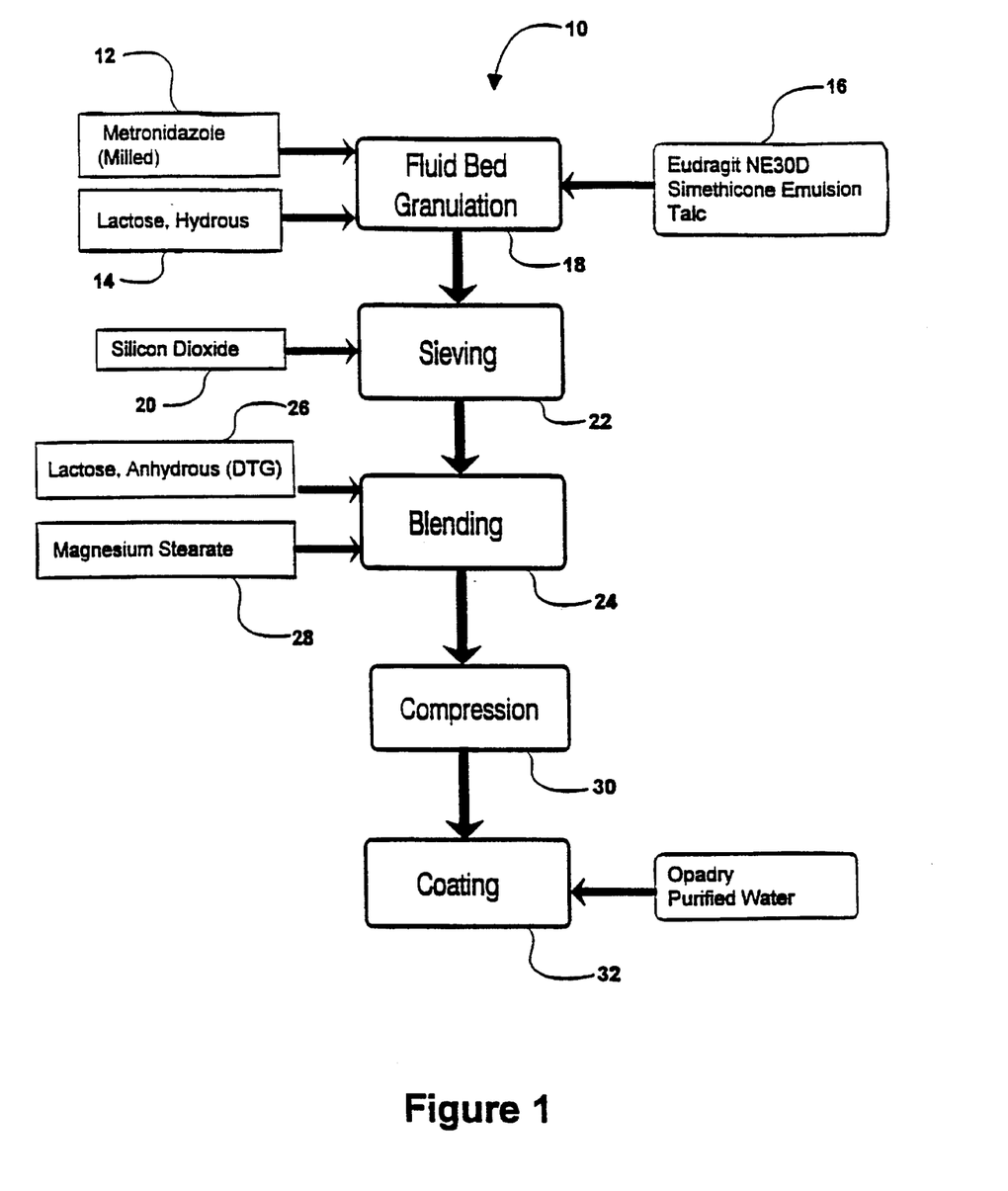
FIG. 1 is a flow diagram representing a preferred method for making modified release metronidazole composition of the invention.

With reference to FIG. 1, an especially preferred method 10 for making the compositions of the invention, utilizing fluid bed granulation, is described. Metronidazole 12 and hydrous lactose 14 are added as dry ingredients into the fluid bed granulator. The dry starting ingredients may have a particle size within a broad range so long as the particles may be suspended by the air flow during granulation. An aqueous suspension 16 comprising an aqueous dispersion of Eudragit® NE30D, talc and optionally simethicone emulsion (antifoam) is produced with gentle stirring to provide the aqueous suspension for spraying during granulation. Fluid bed granulation 18 is carried out as is well known in the art. The granules which are produced are mixed with colloidal silicon dioxide 20, as a glidant, to improve the flow quality and sieved 22 through a screen having a suitable mesh size (e.g., 12–20 mesh), blended 24 in a conventional e.g., twin-shell blender with anhydrous lactose 26 and magnesium stearate (lubricant) 28, conventionally compressed 30 into tablets, and coated 32 with a rapidly dissolving aqueous soluble polymeric film material such as hydroxypropyl methylcellulose polymer, as is well known in the art. The preferred embodiment of the method is exemplified in Example 1, below.

In another of its aspects the present invention entails a method for treating a patient infected with a microorganism which is susceptible to metronidazole, which method comprises administering to a patient having the infection a composition of the invention once daily for a number of days sufficient to eliminate or resolve an infection caused by the microorganisms.

Metronidazole is known to be effective for killing such microorganisms as *Trichomonas vaginalis*, *Entamoeba histolytica*, Helicobacter species, such as *Helicobacter pylori*, anaerobic gram-negative Bacilli, including *Bacteroides fragilis*, *Bacteroides distasonis*, *Bacteroides ovatus*, *Bacteroides thetaiotaomicron*, *Bacteroides vulgatus*, Fusobacterium species, anaerobic gram-positive bacilli including Clostridium species and susceptible strains of Eubacterium, anaerobic grampositive cocci including Peptococcus species and Peptostreptococcus species, and the like.

Among the diseases or conditions which may be treated with once daily administration of the compositions of the present invention are trichomoniasis, bacterial vaginosis and duodenal ulcer disease which is associated with the presence of *Helicobacter pylori*. With respect to *H. pylori*, it is well known to administer metronidazole in combination with other active ingredients such as bismuth and amoxicillin or bismuth and tetracycline. Chiba et al., *Am. J. Gastroenterology*, 87, 1716–1727 (1992); E. Herschel et al., *New England J. Med.*, 328, 308–312 (1993).

A therapeutically effective regimen for treating an infection caused by a microorganism which is susceptible to metronidazole entails once daily oral administration of a composition of the invention which has between about 600 mg metronidazole and about 1000 mg metronidazole, preferably about 750 mg metronidazole for a period of between about 5 days and about 15 days or more. The clinical resolution of the infection or disease is readily determined by a clinician of ordinary skill in the art, such as by microbiological testing or disappearance of clinically characteristic symptoms. The dosage of metronidazole given and/or the length of treatment may be increased or decreased based on the type of infection, the degree of susceptibility of the microorganism to metronidazole, the age and general health of the patient, and like factors of which a clinician of ordinary skill in the art is aware and utilizes in the management of a patient.

The following non-limiting Examples are given by way of illustration.

EXAMPLE 1

PREPARATION OF MODIFIED RELEASE METRONIZADOLE COMPOSITION

This example demonstrates a method for preparing a once-daily metronidazole tablet of the invention, employing fluid bed granulation.

185.13 kg metronidazole (Farchemia, S.P.A., Treviglio, Italy) was milled using a Fitz-Mill fitted with a 40 mesh screen at medium speed, impact forward. The milled metronidazole and 20.55 kg of hydrous lactose (Sheffield, Corp., Norwich, N.Y.) were combined in a Vector Freund, Model #FLF-200 fluid bed granulator (Marion, Iowa), fitted with a single spray arm having 3 nozzles for spraying the coating suspension.

The coating suspension was prepared by combining the following in a mixing tank equipped with a suitable propeller mixer and fluid recycling capability: (i) 20.58 kg of Eudragit® NE30D (30% (w/v) aqueous dispersion) (R öhm Pharma, Weiterstadt, Germany), (ii) 0.08 kg of Simethicone Emulsion (Dow Corning, Midland, Mich.), and (iii) 100 ml of water. After the Eudragit® containing suspension had stirred for several minutes, 3.07 kg of Alphafill 500 Talc (Luzenac America, Englewood, Colo.) was slowly added with mixing over a period of 30 minutes to ensure wetting of the talc particles, importantly, without imparting substantial shear to the Eudragit® polymer. The mixture was mixed and recirculated for an additional 60 minutes to provide a uniform suspension. Alternatively, the above-mentioned mixing tank may be fitted with an Arde Dispershear apparatus (Arde Barinco, Norwood, N.J.), which, in combination with fluid recirculation, should likewise suspend the talc without imparting substantial shear.

The granulator, loaded with the metronidazole and lactose, was run until the inlet air temperature stabilized at 40° C. (about 5 minutes). Once the inlet air temperature stabilized at 40° C., spraying of the coating suspension was begun with the spray gun operated at an atomizing pressure of 50–55 psig and a spray rate of about 600 grams per minute. The coating suspension was maintained with continuous stirring throughout the process. Inlet air temperature for the fluidization air was maintained at approximately 40° C. throughout the granulation process.

When the entire coating suspension had been sprayed, the pump was stopped and fluidization was continued to reduce the moisture content of the granulation to less than 1%. Then the granulator was stopped, 0.25 kg colloidal silicon dioxide (Aerosil 200, Degussa Corporation, Ridgefield Park, N.J.) was added and mixed in by hand. The granulator was restarted and fluidization was continued for an additional 30 seconds to effect mixing.

The granulation was removed from the granulator and sieved by sifting it through a Sprout-Waldron sifter fitted with a 14 mesh screen. The sieved granulation was transferred into a Patterson-Kelly V-blender (30 cubic foot capacity), combined with 32.25 kg anhydrous lactose (direct tablet grade) (Sheffield Corp., Norwich, N.Y.), and the mixture was blended for 10 minutes. Then 2.50 kg of magnesium stearate (Mallinckrodt Chemical, St. Louis, Mo.) was added to the mixture and blended for 5 minutes to provide a metronidazole containing composition suitable for tabletting.

The metronidazole-containing formulation was transferred to the hopper of a Stokes 454 (Stokes-Merrill, Bristol, Pa.) 35-station rotary tablet press which was fitted with 0.750"×0.375"oval shape tablet tooling. The formulation was compressed into tablets at a theoretical weight of 1,013 mg to a thickness of 0.255"and a hardness of about 11 kilopounds.

The compressed tablets were then coated with Opadry. Opadry coating suspension was prepared by mixing 9.60 kg of Opadry Blue YS-1-4256 with 54.4 kg purified water for 30 minutes. The compressed tablets were loaded into a Vector Hi-Coater (Vector Corp., Marion, Iowa) and sprayed with the Opadry suspension at a rate of about 500 g/minute to produce the coated, metronidazole tablets.

EXAMPLE 2

BIOAVAILABILITY OF MODIFIED RELEASE METRONIDAZOLE COMPOSITIONS

This example demonstrates the ability of defined formulations comprising 750 mg of metronidazole to provide, with a single daily dose, bioavailabilty of metronidazole over a 24-hour period, which is comparable to the bioavailability provided by thrice daily doses of immediate release metronidazole (Flagyl®, 250 mg, G. D. Searle & Co., Skokie, Ill.) as determined by the area under the curve (AUC). This example describes two related in vivo studies which measured the plasma metronidazole levels achieved after oral administration of various modified-release formulation. The modified release formulations were made essentially as described in Example 1.

In one in vivo study, nine (9) healthy female volunteers were divided into 3 groups of 3. Three compositions were tested: (i) a modified release composition comprising ethylcellulose (Formulation A), (ii) a modified release composition comprising Eudragit® NE30D (Formulation B), and (iii) Flagyl®, an immediate release metronidazole composition. Plasma metronidazole levels were determined over a 36-hour period, after a single oral administration of the respective compositions. Each individual was administered each of the three formulations. The study was completed over three consecutive weekends to provide a one-week washout period between administrations.

In the other related in vivo study, the protocol was essentially as the above-described study, except as follows. Twelve (12) healthy female volunteers were divided into four groups of three; two Eudragit®-containing formulations (C and D) and two ethylcellulose formulations (E and F) were tested; all individuals received Flagyl (250 mg) and either the two Eudragit®-containing formulations or the two Sureleasee-containing formulations but there was no crossover between the Eudragit®-containing and ethylcellulose-containing formulations. Because of the linear bioavailability kinetics exhibited with Flagyl, the plasma metronidazole levels attained with a 250 mg dose were statistically scaled to a 750 mg dose.

In the in vivo studies, following administration of a formulation, individual plasma metronidazole levels were measured at predetermined times utilizing a validated assay method employing a Supelco-LC-18 high performance liquid chromatography column with UV spectrophotometry at 320 nm being used to detect the concentration of metronidazole. A commercially available software program, PCNONLIN (ClinTrials, Inc., Lexington, Ky. 40504), was used to evaluate the plasma concentration values derived at each timepoint and determine the area under the curve (AUC) and maximum concentration ($C_{max}$) afforded by each of the formulations.

The formulations which were administered are as follows:

|  | mg/tablet | % w/w |
|---|---|---|
| FORMULATION A |  |  |
| Metronidazole USP | 750.0 | 80.95 |
| Microcrystalline Cellulose, PH101 NF | 83.3 | 8.99 |
| Surelease Solids (Ethylcellulose Dispersion, 25% Solids) | 83.3 | 8.99 |
| Simethicone Emulsion USP (Antifoam C Emulsion) | 0.7 | 0.08 |
| Magnesium Stearate NF | 9.2 | 0.99 |
|  | 926.5 |  |
| FORMULATION B |  |  |
| Metronidazole USP | 750.0 | 82.79 |
| Microcrystalline Cellulose, PH101 NF | 83.3 | 9.20 |
| Eudragit NE30D Solids (Acrylic Resin, 25% Solids) | 41.7 | 4.60 |
| Talc USP (500 mesh) | 20.8 | 2.30 |
| Simethicone Emulsion USP (Antifoam C Emulsion) | 0.3 | 0.03 |
| Colloidal Silicon Dioxide NF | 0.8 | 0.09 |
| Magnesium Stearate NF | 9.0 | 0.99 |
|  | 905.9 |  |
| FORMULATION C |  |  |
| Metronidazole USP | 750.0 | 74.05 |
| Lactose, Hydrous NF | 83.3 | 8.22 |
| Eudragit NE30D Solids (Acrylic Resin, 30% Solids) | 25.0 | 2.47 |
| Talc USP (500 mesh) | 12.5 | 1.23 |
| Simethicone Emulsion USP (Antifoam C Emulsion) | 0.3 | 0.03 |
| Lactose, Anhydrous (DTG) NF | 130.7 | 12.90 |
| Colloidal Silicon Dioxide NF | 1.0 | 0.10 |
| Magnesium Stearate NF | 10.0 | 0.99 |
|  | 1012.8 |  |
| FORMULATION D |  |  |
| Metronidazole USP (20% of Metronidazole added neat) | 750.0 | 72.99 |

|  | mg/tablet | % w/w |
|---|---|---|
| Lactose, Hydrous NF | 66.6 | 6.48 |
| Eudragit NE30D Solids | 20.0 | 1.95 |
| (Acrylic Resin, 30% Solids) | | |
| Talc USP (500 mesh) | 10.0 | 0.97 |
| Simethicone Emulsion USP | 0.3 | 0.03 |
| (Antifoam C Emulsion) | | |
| Lactose, Anhydrous (DTG) NF | 169.4 | 16.49 |
| Colloidal Silicon Dioxide NF | 1.0 | 0.10 |
| Magnesium Stearate NF | 10.2 | 0.99 |
|  | 1027.5 | |
| FORMULATION E | | |
| Metronidazole USP | 750.0 | 71.10 |
| (20% of Metronidazole added neat) | | |
| Microcrystalline Cellulose, PH101 NF | 66.6 | 6.31 |
| Surelease Solids | 53.3 | 5.05 |
| (Ethylcellulose Dispersion, 25% Solids) | | |
| Simethicone Emulsion USP | 0.5 | 0.05 |
| (Antifoam C Emulsion) | | |
| Microcrystalline Cellulose, PH102 NF | 174.0 | 16.50 |
| Magnesium Stearate NF | 10.4 | 0.99 |
|  | 1054.8 | |
| FORMULATION F | | |
| Metronidazole USP | 750.0 | 71.70 |
| Microcrystalline Cellulose, PH101 NF | 83.3 | 7.96 |
| Surelease Solids | 66.7 | 6.38 |
| (Ethylcellulose Dispersion, 25% Solids) | | |
| Simethicone Emulsion USP | 0.6 | 0.06 |
| (Antifoam C Emulsion) | | |
| Microcrystalline Cellulose, PH102 NF | 135.0 | 12.91 |
| Magnesium Stearate NF | 10.4 | 0.99 |
|  | 1046.0 | |

Figure 2:
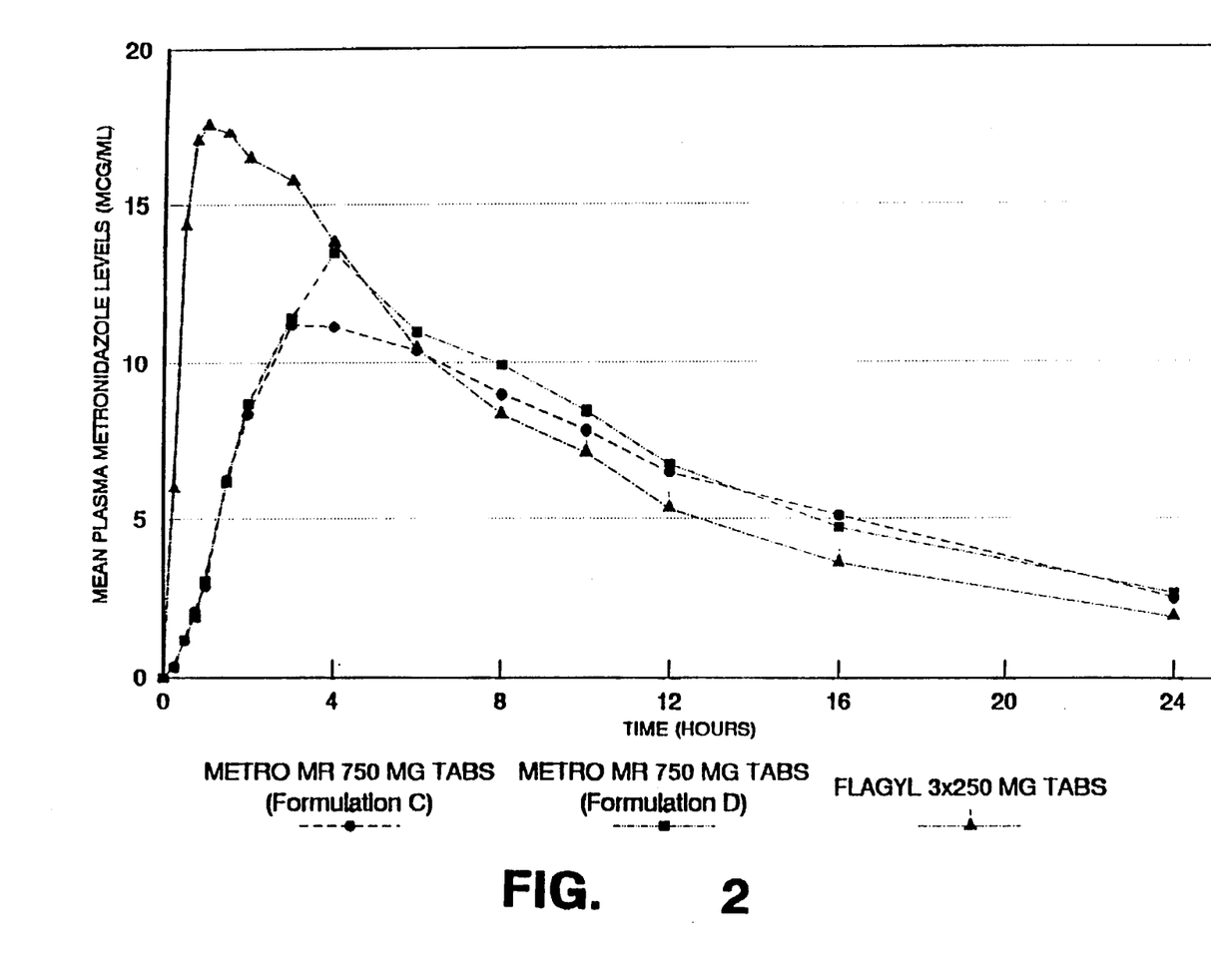
FIG. 2 is a graphical depiction of the bioavailability of a commercially available immediate release metronidazole composition, a modified release metronidazole composition comprising 2.47 wt % poly(meth)acrylic acid ester (formulation C) showing very good bioavailability, and a modified release metronidazole composition comprising 1.95 wt % poly(meth)acrylic acid ester (formulation D) showing very good bioavailability.
Figure 3:
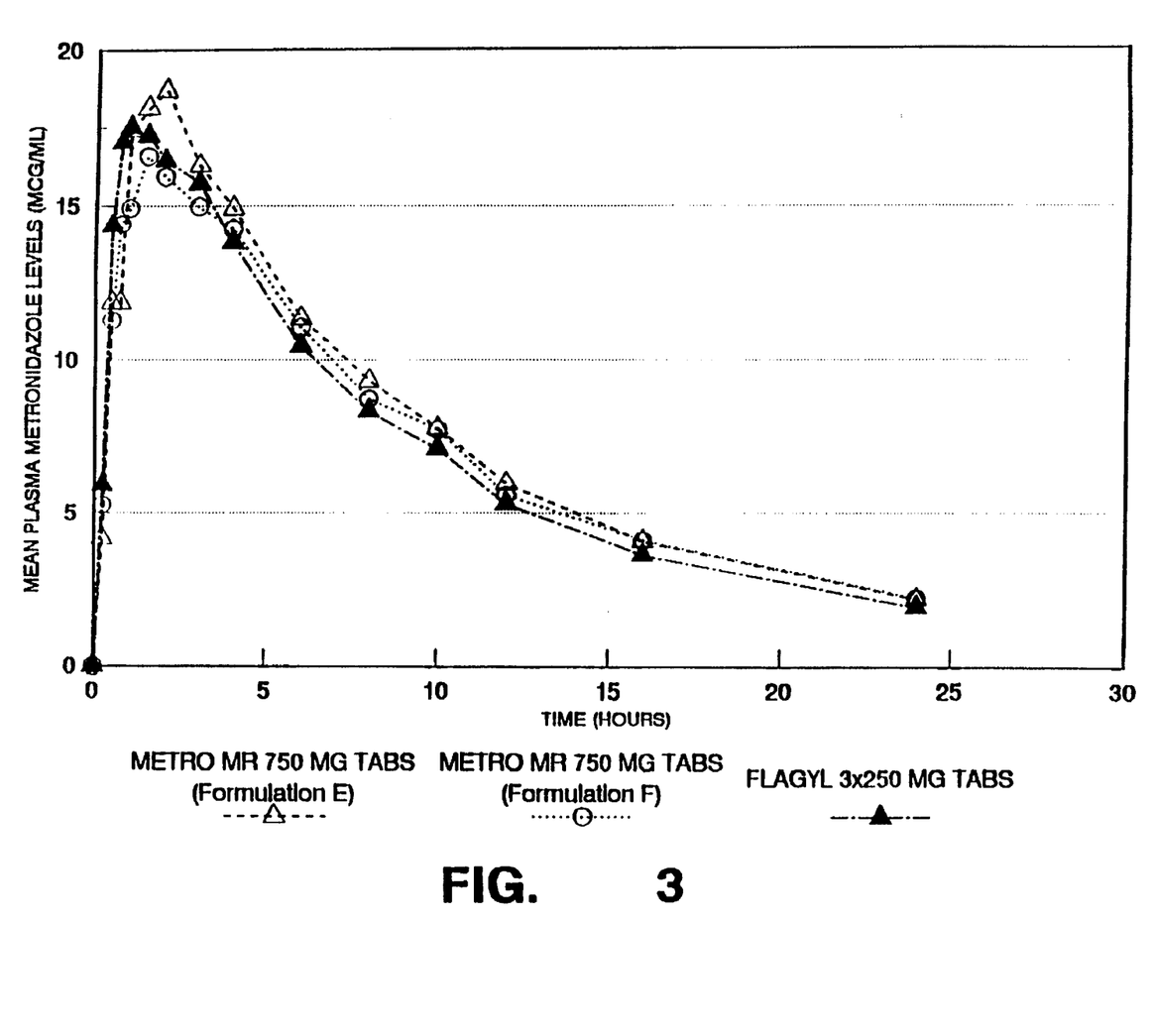
FIG. 3 is a graphical depiction of the bioavailability (for comparison to FIG. 2) of a commercially available immediate release metronidazole composition, a metronidazole composition comprising 5.05 wt % ethylcellulose as a release agent (formulation E) showing very poor modified release characteristics, and 6.38 wt % ethylcellulose as a release agent (formulation F), also showing very poor modified release characteristics.
Figure 4:
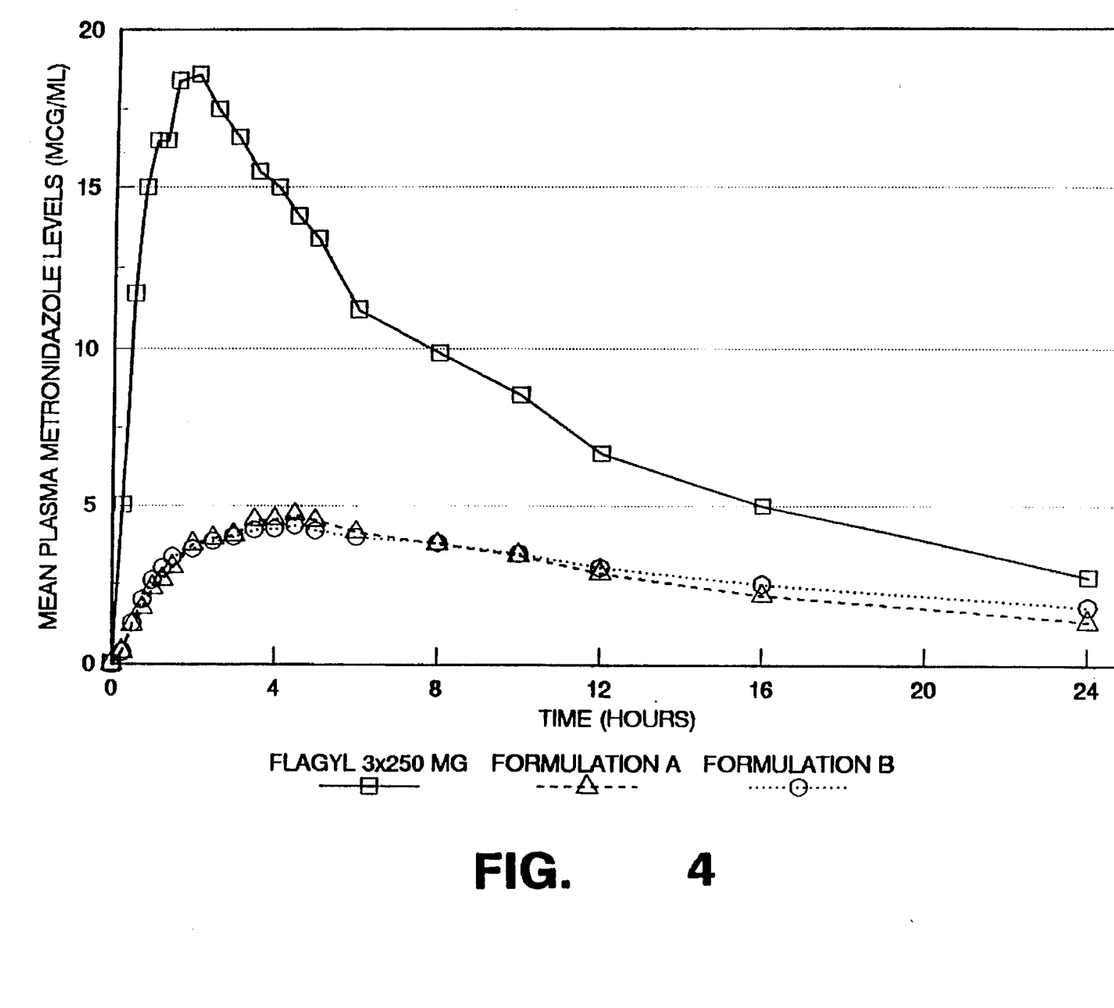
FIG. 4 is a graphical depiction of the bioavailability (for comparison to FIG. 2) of a commercially available immediate release metronidazole composition, a modified release composition comprising 8.99 wt % ethylcellulose dispersion as the release agent, showing poor bioavailability (formulation A) and a modified release metronidazole composition comprising 4.6 wt % poly(meth)acrylic acid ester as the release agent also showing poor bioavailability (formulation B)

The results of the studies are depicted graphically in FIGS. 2–4.

Formulations C and D, which comprise 2.47% and 1.95% Eudragit® NE30, respectively, provided bioavailability of metronidazole over 24 hours which was substantially equivalent to that of the immediate release Flagyl®, as determined by the PCNONLIN program. The ratio of $AUC_{(formulation\ C)}:AUC_{(Flagyl®)}$ was 0.961, and the ratio of $AUC_{(formulation\ D)}:AUC_{(Flagyl®)}$ was 1.01. Also these compositions exhibited desirable modified release characteristics; plasma metronidazole levels were maintained between about 2.5 mcg/ml and about 13.5 mcg/ml over the entire 24-hour period (FIG. 2).

As FIG. 3 demonstrates, the ethylcellulose-containing compositions, Formulations E and F, exhibited poor release characteristics. While the bioavailability of the ethylcellulose-containing compositions was similar to Flagyl®—the ratio of $AUC_{(formulation\ E)}:AUC_{(Flagyl®)}$ was 1.07, and the ratio of $AUC_{(formulation\ F)}:AUC_{(Flagyl®)}$ was 1.02—the composition of Formulations E and F exhibited substantially no modified release characteristics.

FIG. 4 demonstrates that Formulation A (comprising ~9% Sureleas®) and Formulation B (comprising 4.6% Eudragit® NE30D) were able to slow the release of metronidazole, but only at the cost of greatly reducing the bioavailability of metronidazole. The ratio of $AUC_{(formulation\ A)}:AUC_{(Flagyl®)}$ was 0.357, and the ratio of $AUC_{(formulation\ B)}:AUC_{(Flagyl®)}$ was 0.397. Thus, these compositions were able to provide only about 35%–40% bioavailability of metronidazole, compared to Flagyl®.

In view of the above it will be seen that the compositions of the invention importantly provide bioavailability of metronidazole which is comparable to Flagyl®, while at the same time exhibiting a controlled rate of release so that plasma metronidazole levels are Flagyl®, while at the same time exhibiting a controlled rate of release so that plasma metronidazole levels are not caused to spike, but rather are maintained at levels of between about 2.5 mcg/ml and 13.5 mcg/ml over a 24 hour period, which provides sustained therapeutic effectiveness.

EXAMPLE 3

IN VITRO DISSOLUTION OF MODIFIED RELEASE METRONIDAZOLE COMPOSITIONS

This example demonstrates the rate of in vitro dissolution of modified release metronidazole tablets comprising poly-(meth)acrylic acid ester. The dissolution rates for the compositions of the invention correlate to the in vivo bioavailability of metronidazole formulations comprising poly(meth)acrylic acid ester.

The dissolution tests were performed using the standard USP XXII Dissolution Apparatus 2 (paddles), run at 50 RPM, in Deionized Water at 37° C. for 12 hours. Five modified release formulations containing 750 mg metronidazole, and an immediate release formulation (Flagyl®, 3×250 mg.) as a control were tested. Three of the modified release formulations were Formulation B, Formulation C and Formulation D which are disclosed in Example 2, above. The other two modified release formulation are as follows:

|  | mg/tablet | % w/w |
|---|---|---|
| FORMULATION G | | |
| Metronidazole USP | 750.0 | 78.48 |
| (10% of metronidazole added neat) | | |
| Lactose, Hydrous NF | 75.0 | 7.85 |
| Eudragit NE30D Solids | 22.5 | 2.35 |
| (Acrylic Resin, 30% Solids) | | |
| Talc USP (500 mesh) | 11.3 | 1.18 |
| Simethicone Emulsion USP | 0.3 | 0.03 |
| (Antifoam C Emulsion) | | |
| Lactose, Anhydrous (DTG) NF | 86.0 | 9.00 |
| Colloidal Silicon Dioxide NF | 1.0 | 0.10 |
| Magnesium Stearate NF | 9.5 | 0.99 |
|  | 955.6 | |
| FORMULATION H | | |
| Metronidazole USP | 750.0 | 77.42 |
| Lactose, Hydrous NF | 83.3 | 8.60 |
| Eudragit NE30D Solids | 25.0 | 2.58 |
| (Acrylic Resin, 30% Solids) | | |
| Talc USP (500 mesh) | 12.5 | 1.29 |
| Simethicone Emulsion USP | 0.3 | 0.03 |
| (Antifoam C Emulsion) | | |
| Lactose, Anhydrous (DTG) NF | 87.1 | 8.99 |
| Colloidal Silicon Dioxide NF | 1.0 | 0.10 |
| Magnesium Stearate NF | 9.6 | 0.99 |
|  | 968.7 | |

Figure 5:
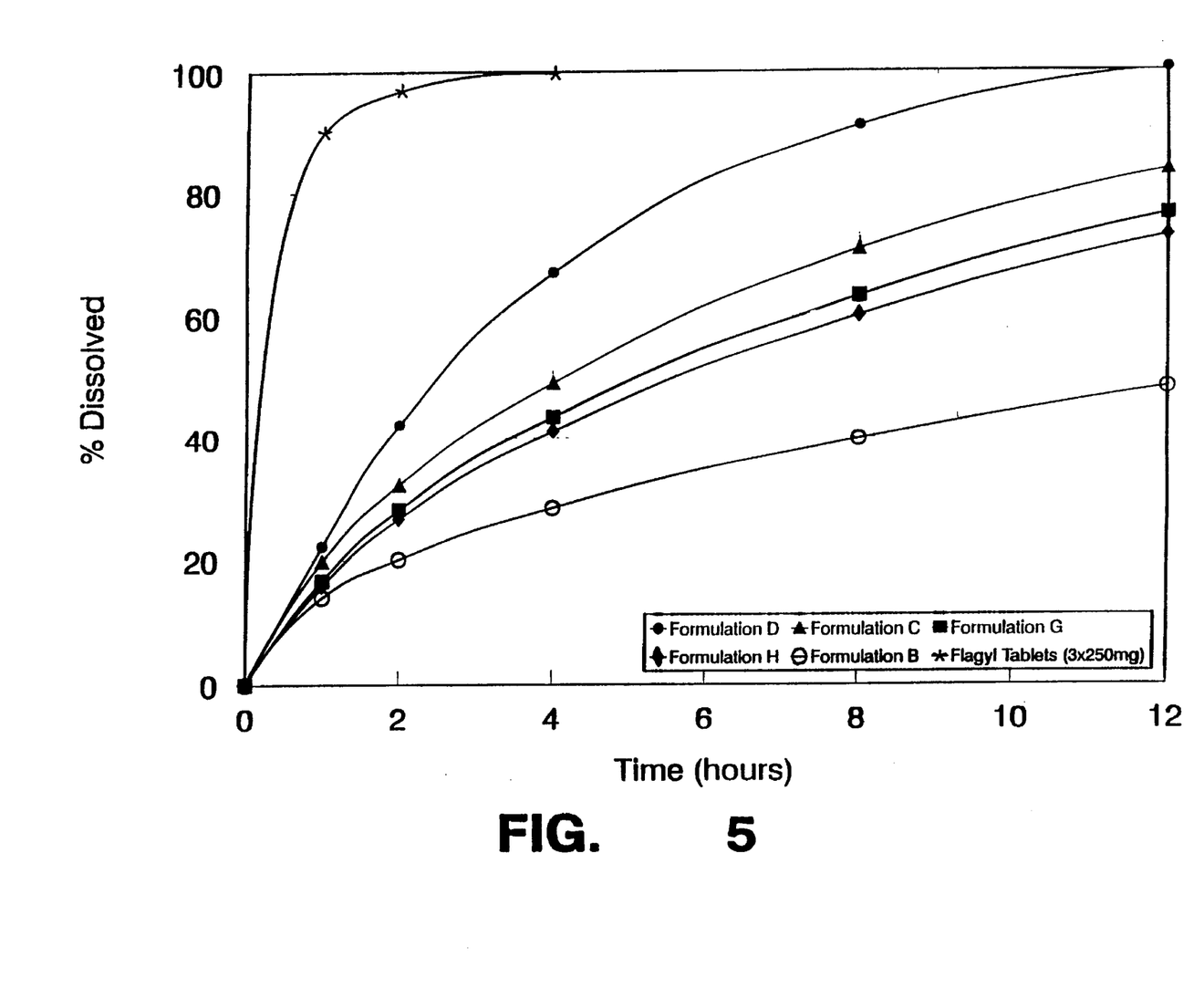
FIG. 5 is a graphical depiction of in vitro dissolution rates for modified release metronidazole compositions comprising poly(meth)acrylic acid ester.

The dissolution data are depicted graphically in FIG. 5. As a comparison FIG. 5 to FIGS. 2–4 demonstrates, desirable in vitro release rates for modified release metronidazole compositions of the invention, as compared to immediate release metronidazole (Flagyl®), correlated well to in vivo bioavailability.

While the present invention has been described in some detail by way of illustration and examples, modifications which may be apparent to those having ordinary skill in the art are intended to be within the scope of the following claims.

We claim:

1. A method for making a modified release metronidazole composition, the method comprising the steps of:

(a) contacting in a fluid bed granulator, under conditions suitable for producing granules, (1) a dry mixture comprising from about 59 to about 79 parts by weight of a first portion of metronidazole and optionally up to 23 parts by weight of a first aqueous soluble diluent with (2) an aqueous suspension comprising from about 1.5 to about 3.0 parts by weight of an aqueous insoluble, pH-independent, aqueous expandable polymethacrylic acid ester copolymer, and an effective amount of a detackifying agent;

(b) combining the granules produced in step (a) with an effective amount of a pharmaceutically acceptable glidant;

(c) if necessary, particle-sizing the mixture of (b) to provide a mixture with a substantially uniform particle size suitable for compressing into tablet form;

(d) optionally blending the mixture with up to about 20 parts by weight of a second portion of metronidazole;

(e) blending the mixture with up to 23 parts by weight of a second aqueous soluble diluent and an effective amount of a pharmaceutically acceptable lubricant; and (f) compressing a predetermined amount of the blended mixture of step (e) to produce a tablet;

wherein the percentage of metronidazole provided by (a)(1) and (d) is from about 72% to about 79% by weight, based on the total weight of the tablet, and wherein the percentage of aqueous soluble diluent provided by (a)(1) and (e) is from about 16% and about 23% by weight, based on the total weight of the tablet.

2. A method according to claim 1, wherein the first aqueous soluble diluent is present in an amount of from about 5% and about 11% by weight and the second aqueous soluble diluent is present in an amount of from about 8% and about 18% by weight.

3. A method according to claim 2, wherein the first aqueous soluble diluent is present in an amount of from about 6% and about 9% by weight and the second aqueous soluble diluent is present in an amount of from about 12% and about 17% by weight.

4. A method according to claim 3, wherein the first aqueous soluble diluent and the second aqueous soluble diluent are lactose.

5. A method according to claim 1 wherein the detackifying agent is talc.

6. A method according to claim 1 wherein the glidant is silicon dioxide and is present in amount of about 0.1% by weight.

7. A method according to claim 1 wherein the lubricant is magnesium stearate and is present in amount of about 1% by weight.

8. A method according to claim 1 wherein the aqueous suspension of (a)(ii) further comprises an amount of an antifoam agent effective to reduce foaming during step (a).

9. A method according to claim 1 which further comprises (g) coating the tablet with an aqueous soluble polymeric coating.

* * * * *

UNITED STATES PATENT AND TRADEMARK OFFICE
CERTIFICATE OF CORRECTION

PATENT NO.    : 5,618,559
DATED         : April 8, 1997
INVENTOR(S)   : SUBHASH DESAI ET AL.

It is certified that error appears in the above-identified patent and that said Letters Patent is hereby corrected as shown below:

COLUMN 1

Line 5, "Application" should read --application--.

COLUMN 4

Line 23, "of" should read --of the--.

COLUMN 5

Line 48, "may" should read --may be--.

COLUMN 7

Line 61, "gram-positive" should read --Gram-positive--; and
    Line 63, "grampositive" should read --gram-positive--.

COLUMN 8

Line 47, "(R" should be deleted; and
    Line 48, "öhm" should read --(Röhm--.

COLUMN 10

Line 17, "were-" should read --were--.

UNITED STATES PATENT AND TRADEMARK OFFICE
CERTIFICATE OF CORRECTION

PATENT NO.    : 5,618,559

DATED         : April 8, 1997

INVENTOR(S)   : SUBHASH DESAI ET AL.

It is certified that error appears in the above-identified patent and that said Letters Patent is hereby corrected as shown below:

<u>COLUMN 14</u>

```
Line 17, "claim 1" should read --claim 1,--;
Line 19, "claim 1" should read --claim 1,--;
Line 20, "in" should read --in an--;
Line 22, "claim 1" should read --claim 1,--;
Line 23, "in" should read --in an--; and
Line 25, "claim 1" should read --claim 1,--.
```

Signed and Sealed this

Twenty-sixth Day of September, 2000

Attest:

Q. TODD DICKINSON

*Attesting Officer*     *Director of Patents and Trademarks*